United States Patent [19]
Brucher et al.

[11] Patent Number: 5,167,165
[45] Date of Patent: Dec. 1, 1992

[54] DEVICE FOR POSITIONING A MEASURING ELEMENT

[75] Inventors: Rainer Brucher, Uhldingen; Thomas Barenbach, Radolfzell/Möggingen, both of Fed. Rep. of Germany

[73] Assignee: Eden Medizinische Elektronik GmbH, Überlingen, Fed. Rep. of Germany

[21] Appl. No.: 810,705

[22] Filed: Dec. 17, 1991

[30] Foreign Application Priority Data

Dec. 17, 1990 [DE] Fed. Rep. of Germany ....... 4040307

[51] Int. Cl.⁵ .............................................. A61B 8/00
[52] U.S. Cl. .................................. 74/479; 128/660.09; 128/662.03
[58] Field of Search ................. 33/438, 441, 511, 512, 33/25.3; 128/660.09, 662.03, 95.1, 99.1; 73/861.25, 861.26, 861.28; 414/917, 744.2; 901/14, 24, 41; 74/479

[56] References Cited

U.S. PATENT DOCUMENTS

| | | | |
|---|---|---|---|
| 3,470,868 | 10/1969 | Krause et al. | 128/660.09 |
| 3,805,596 | 4/1974 | Klahr | 128/660.09 |
| 4,399,822 | 8/1983 | Theumer | 128/660.09 |
| 4,817,621 | 4/1989 | Aaslid | 128/662.03 |
| 5,022,401 | 6/1991 | Eden | 128/662.03 |

Primary Examiner—Kyle L. Howell
Assistant Examiner—George Manuel
Attorney, Agent, or Firm—Robert W. Becker & Associates

[57] ABSTRACT

A device for positioning a measuring element is provided in which the measuring element is suspended by two parallelogram linkage systems in a pivotable manner, the parallelogram linkage systems being arranged at an angle relative to one another. Each lever of the parallelogram linkage systems is provided with a ball joint and is drivingly connected via the ball joint to a respective threaded spindle. The threaded spindles are drivable by a reversible stationary stepping motor. With this arrangement it is possible for the measuring element to perform planar and circular movements in addition to the commonly performed pivoting movements. Furthermore, an adjustment of the pivoting point is possible, and each individual lever of the parallelogram linkage system may be adjusted individually.

16 Claims, 4 Drawing Sheets

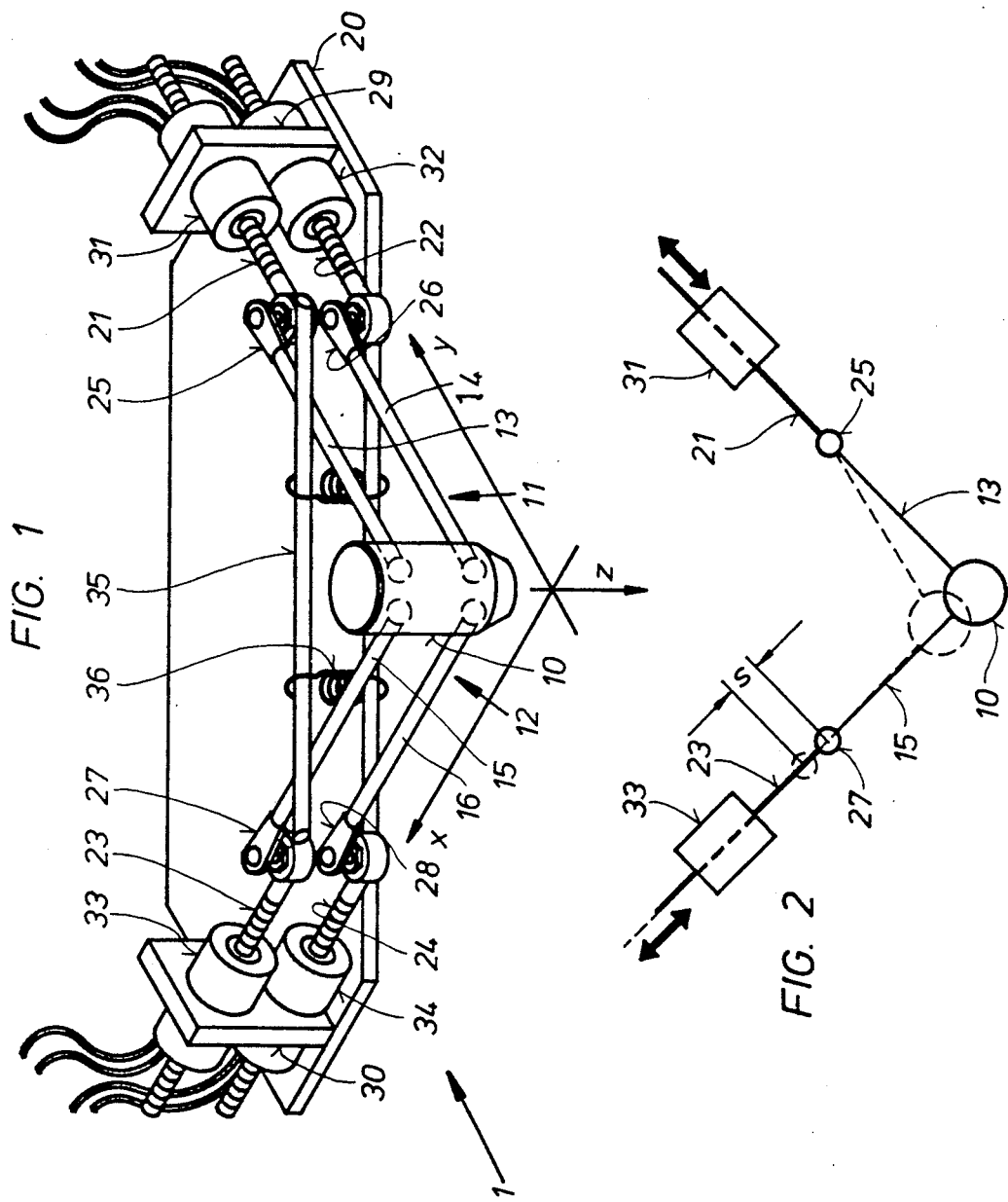

DEVICE FOR POSITIONING A MEASURING ELEMENT

BACKGROUND OF THE INVENTION

The present invention relates to a device for positioning a measuring element, for example, in the form of a doppler signal emitter and/or receiver for determining the position of a blood vessel and flow direction of the flowing blood wherein the measuring element is suspended by two parallelogram linkage systems that are arranged at an angle relative to one another such that the measuring element is movable in a random fashion about an adjustable point.

Such a device has been known from U.S. Pat. No. 4,817,621. The parallelogram linkage systems, with free ends thereof, are respectively pivotably supported at a reference plate whereby the parallelogram linkage systems are arranged relative to one another at a prescribed angle. When an examination is performed the parallelogram linkage systems are directly positioned at selected locations of the head of a patient. This device has been proven successful, however, the constructive expenditure is substantial, especially, because of the plurality of joints that are required. An economic manufacture is thus not possible and, furthermore, disruptions of the examinations do occur because the measuring element will not maintain its initial position. Furthermore, it is disadvantageous that the measuring element, since it is geometrically and mechanically fixed, may only perform pivoting movements about a fixed pivoting point. Also, examinations may only be performed when the patient is in a lying position so that not all locations of the head may be examined. Furthermore, the handling of the aforementioned device is difficult due to the substantial mass and weight of the device. A further restriction of the application of the aforementioned device is that a patient, during an examination, may not move his head because this may lead to incorrect results and requiring a correction of the position of the measuring element.

It is therefore an object of the present invention to provide a device for positioning a measuring element of the aforementioned kind which is of a simple construction and is thus economical to manufacture, and allows an uninterrupted operation. It is especially important that the measuring element may be aligned with certain location and may easily be positioned whereby the once attained position should be maintained during examination without having to correct the position so that examinations may be performed over an extended period of time. Furthermore, such examinations should be performable in any position of the patient, especially in a sitting position. It is also desirable that the device be mountable without difficulties on a holding device which is attached to the head of the patient so that movements of the head will not influence the position of the measuring element. A further object of the present invention is to provide the device such that planar and circular movements may be performed, that the pivoting point about which random movement occurs may be adjustable and that the movement of the measuring element may be programmable in a simple manner.

BRIEF DESCRIPTION OF THE DRAWINGS

This object, and other objects and advantages of the present invention, will appear more clearly from the following specification in conjunction with the accompanying drawings, in which:

FIG. 1 is a perspective representation of the inventive device in which the measuring element is directly connected with the stepping motors in a driving connection via the parallelogram linkage system and via threaded spindles;

FIG. 2 shows a plan view of the device according to FIG. 1 in a schematic representation;

SUMMARY OF THE INVENTION

Figure 3:
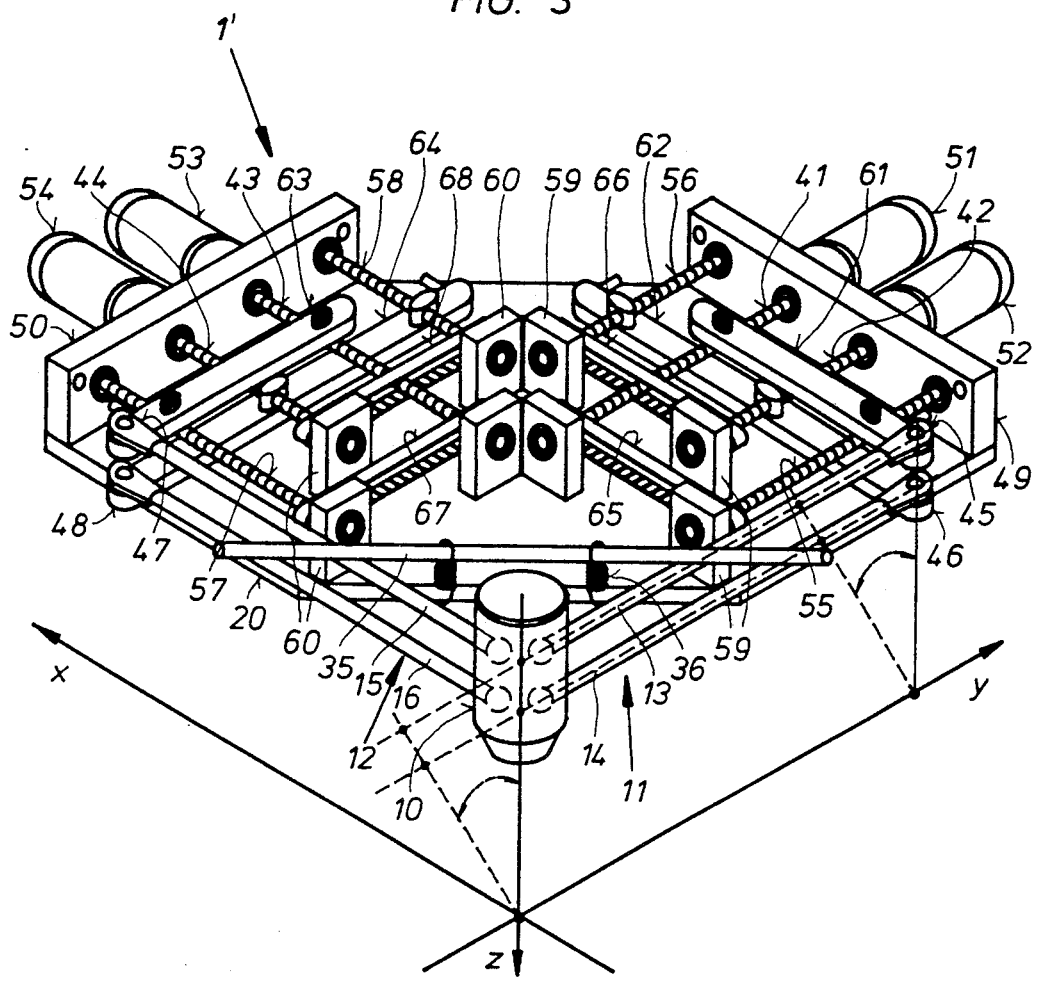
FIG. 3 shows a perspective representation of the device according to FIG. 1 with intermediate members provided between the levers of the parallelogram linkage system and the threaded spindles.
Figure 4:
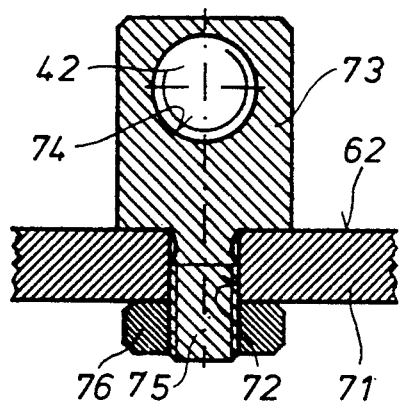
FIG. 4 shows the connection of the intermediate members and the threaded spindles according to FIG. 3 in a cross-sectional view.
Figure 5:
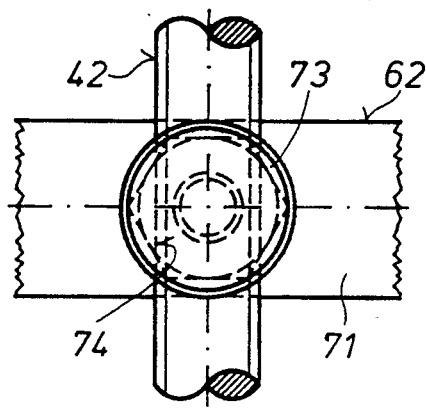
FIG. 5 is a plan view of the embodiment according to FIG. 4.

The device for positioning a measuring element of the present invention is primarily characterized by two parallelogram linkage systems by which the measuring element is suspended in a pivotable manner, the parallelogram linkage system being arranged at an angle relative to one another; the parallelogram linkage systems comprising levers and respective ball joints connected to the levers, the levers being in a drivable connection with respective first threaded spindles via the ball joints; and reversible stationary stepping motors for driving the first threaded spindles. The levers may be directly connected to the first threaded spindles or they may be connected by intermediate members to the first threaded spindles.

The intermediate members may be in the form of adjustable slides. It is advantageous that the device further comprises second threaded spindles for guiding the adjustable slides, whereby the second threaded spindles are spaced at a distance from the first threaded spindles and are synchronously drivable relative to the first threaded spindles. In a preferred embodiment the device further comprises drive means for driving the second threaded spindles, whereby the drive means are drivingly connected to the first and second threaded spindles. The drive means may be, for example, in the form of a belt drive In another advantageous embodiment the device further comprises a base plate on which the stepping motors are supported, and wherein the first threaded spindles extend parallel to the base plate, with respective pairs of the first threaded spindles being perpendicular to one another.

It is preferable that the first threaded spindles penetrate the stepping motors and are directly drivable by the stepping motors.

It is expedient to arrange the first threaded spindles in pairs parallel to the stepping motors, whereby the first threaded spindles are drivable by the stepping motors by a driving means. The driving means may be a belt drive. Furthermore, the device may comprise holders connected to the base plate for supporting the stepping motors whereby the stepping motors are arranged in pairs. It is expedient that the first threaded spindles are pivotably supported at the holders. Supporting elements may be provided that are connected to the base plate for supporting in a pivotable manner the first threaded spindles. It is advantageous to pivotably support the first threaded spindles at the holders.

The base plate may be provided with a recess in the area of the measuring element.

It is expedient to further provide the device with spring means for connecting at least one of the parallelogram linkage systems to the base plate in a springed manner. The spring means comprises a rail and at least one spring whereby the spring supports the rail at the base plate.

With the inventive device for positioning a measuring element a simple construction and thus an economic manufacture is provided. Furthermore, the device is easy to handle and the device allows pivoting movements as well as planar and circular movements of the measuring element and an adjustment of the pivoting point. This is achieved since each lever of the parallelogram linkage system has coordinated therewith a reversible stepping motor that is connected to the lever via a ball joint so that each individual lever of the parallelogram linkage system may be adjustable within given limits, and the measuring element may thus perform any desired movement. The detection of a measuring point, for example, a window in the skull of a patient and/or the alignment of the measuring element with a blood vessel, are thus substantially facilitated.

Furthermore, it is possible to program each individual stepping motor separately so that the measuring element may perform all kinds of movements. In dependency of the respective angle of rotation of the stepping motors as well as of the pitch of the threaded spindles high precision movements, respectively, positioning are possible. An extremely versatile applicability of the device combined with a high operational safety and a simple handling is thus provided.

DESCRIPTION OF PREFERRED EMBODIMENTS

The present invention will now be described in detail with the aid of several specific embodiments utilizing FIGS. 1 through 8.

The device 1 represented in FIG. 1 serves to position a measuring element 10 on the head of a patient, for example, in order to determine the position of a blood vessel and/or the flow direction of the flowing blood through a window in the skull. For this purpose, the device 1 is inserted into a special holding means and the measuring element 10 is aligned with the window.

In order to adjust the position of the measuring element in a quick and exact manner the measuring element is suspended by two parallelogram linkage systems 11 and 12. The levers 13, 14, 15, and 16 of the parallelogram linkage systems 11 and 12 are connected via ball joints 25, 26, 27, and 28 to a rotatably supported first threaded spindle 21, 22, 23 and 24. Electrical stepping motors 31, 32, 33, and 34 serve to adjust the first threaded spindles 21 to 24, whereby the stepping motors 31 to 34 are supported at holders 29 and 30 supported at a base plate 20. The first threaded spindles 21 to 24 penetrate the respective coordinated stepping motor 31 to 34 so that adjustment movements of the stepping motors are directly transmitted to the threaded spindles. A rail 35 is supported by the levers 13 and 15 of the parallelogram linkage systems 11 and 12, the rail 35 being connected in a springed manner via two prestressed tension springs 36 to the base plate 20. Due to the rail 35 that is supported in a springed manner, the parallelogram linkage systems 11 and 12 exert a constant pressure on the measuring element 10 when adjustment movements occur.

With the aid of the stepping motors 31 to 34 the measuring element 10 may be adjusted in the direction of the axes x, y, and z (see FIG. 1) since the stepping motors 31 to 34 may be controlled individually and/or differently. The measuring element 10 may thus perform all kinds of movements within, the ranges indicated in FIG. 2 as the corresponding travel distance for adjustments. Thus, not only pivoting movements may be performed, but also planar and circular movements of the measuring element 10. The detection of a window and the alignment of the measuring element 10 with the window is thus very simple. Of course, these adjustment movements may also be programmable so that they are easily reproducible.

In the device 1' according to FIG. 3 the first threaded spindles 41, 42, 43, and 44, which are supported via holders 49 and 50 at the base plate 20 and are drivable by the stepping motors 51, 52, 53, and 54, are drivingly connected to the levers 13, 14, 15, and 16 of the parallelogram linkage systems 11 and 12 via intermediate members in the form of slides 61, 62, 63, and 64. The slides 61-64, at their free ends, are provided with ball joints 45, 46, 47 and 48. The individual adjustment movements of the stepping motors 51, 52, 53, and 54, which are also individually supported at the holders 49 and 50, are thus transmitted via the aforementioned components to the measuring element 10.

Figure 6:
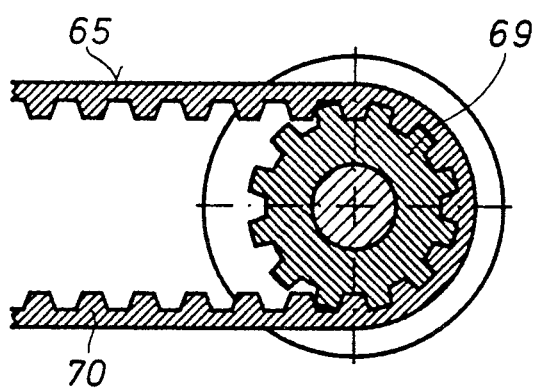
FIG. 6 is a detail of the driving connection between the two threaded spindles of the embodiment according to FIG. 3 in a cross-sectional view.
Figure 7:
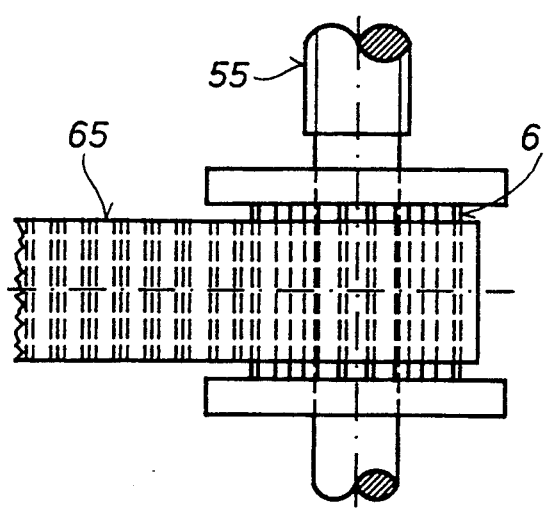
FIG. 7 is a plan view of the embodiment according to FIG. 6.

In order to ensure that the slides 61, 62, 63, and 64 will not cant or tilt, but are reliably guided, second threaded spindles 55, 56, 57, and 58 are provided which rotate synchronously relative to the threaded spindles 41, 42, 43, and 44 and on which the slides 61 to 64 are adjustably guided. The driving connection of the threaded spindles 41 and 55, 42 and 56, 43 and 57, as well as 44 and 58 is provided by a respective belt drive 65, 66, 67, and 68, as shown in FIGS. 6 and 7. The individual belt drives 65 to 68 are comprised of a toothed disk 69 which is fixedly connected to the respective threaded spindle and a toothed belt 70 which engages the toothed disk 69. The free ends of the threaded spindles 41, 42, 55, and 56 are rotatably supported at supporting elements 59 and the free ends of the threaded spindles 42, 44, 57 and 58 are rotatably supported at the supporting elements 60.

The slides 61 to 64 are comprised of a plate 71 and a member 73 in the form of a bolt which, with a threaded portion 75 thereof extends through a bore 72 provided at the plate 71. The members 73 which are provided with a respective threaded bore 74 for receiving the threaded spindles 41 to 44, respectively, 55 to 58 are clamped to the plate 71 by a respective nut 76.

When an adjustment movement occurs, for example, at the threaded spindle 42, the second threaded spindle 56 is synchronously driven via the belt drive 66 so that the slide 62, which is slidably supported at the first threaded spindle 42 and the second threaded spindle 56, is moved. The adjustment movement of the slide 62 is transmitted via the ball joint 46 to the lever 14 of the parallelogram linkage system 11 so that the measuring element 10 to which the lever 14 is connected is correspondingly moved and displaced to a certain extent.

Figure 8:
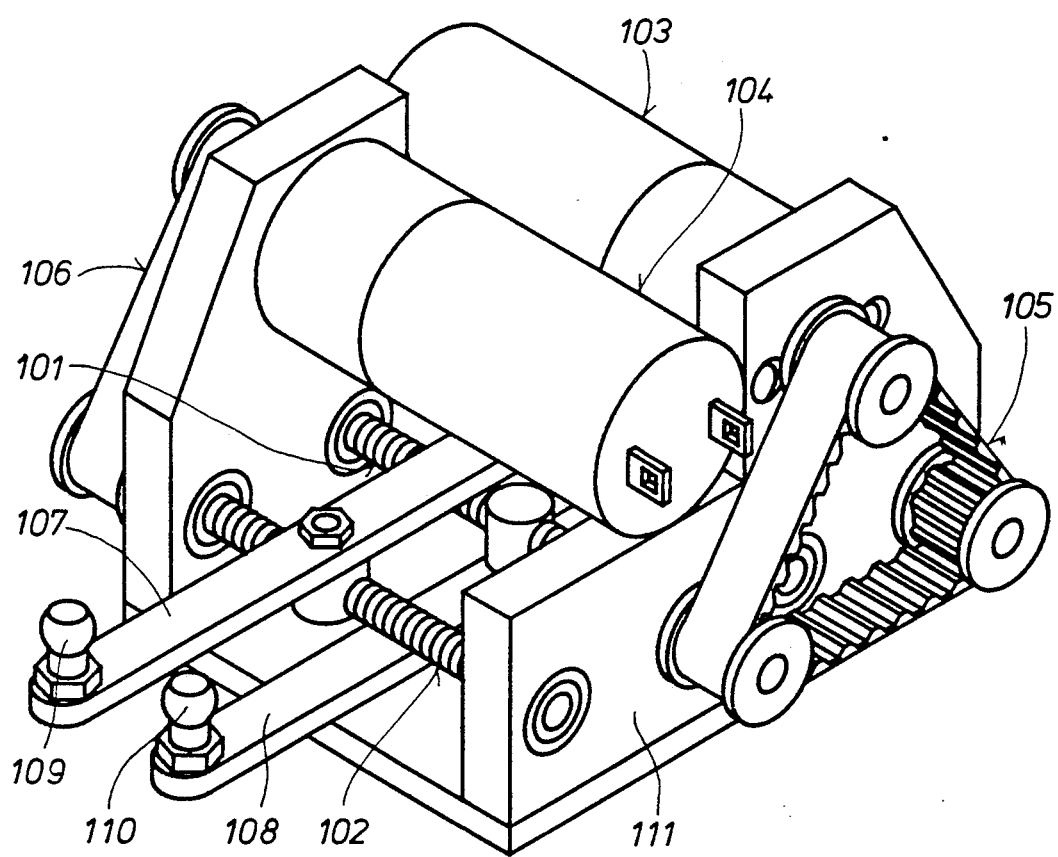
FIG. 8 shows a different arrangement of the stepping motors of a device according to FIG. 3.

In the embodiment represented in FIG. 8 the stepping motors 103 and 104 which serve to drive the first threaded spindles 101 and 102 within a device according to, for example, FIG. 3, are arranged axis-parallel to the first threaded spindles 101 and 102 at a holder 111. The stepping motors 103 and 104 are drivingly connected via a drive means in the form of a belt drive 105 and 106 to the first threaded spindles 101 and 102.

The adjustment movements of the first threaded spindles 101 and 102 are again transmitted via slides 107, 108 which are connected via ball joints 109 and 110 to the levers of the parallelogram linkage systems. Second threaded spindles, which are not shown in the drawing, are provided for the exact guidance of the slides 107 and 108, the second threaded spindles being synchronously drivable via the belt drives 105 and 106 relative to the threaded spindles 101 and 102.

The present invention is, of course, in no way restricted to the specific disclosure of the specification and drawings, but also encompasses any modifications within the scope of the appended claims.

What we claim is:

1. A device for positioning a measuring element, comprising:
    two parallelogram linkage systems by adapted for positioning measuring element in a pivotable manner, said parallelogram linkage systems arranged at an angle relative to one another;
    said parallelogram linkage systems comprising levers and respective ball joints connected to said levers, said levers being in a drivable connection with respective first threaded spindles via said ball joints; and
    reversible stationary stepping motors connected to said spindles for driving said first threaded spindles.

2. A device for positioning a measuring element according to claim 1, further comprising intermediate members for connecting said levers to said first threaded spindles.

3. A device for positioning a measuring element according to claim 2 wherein said intermediate members are adjustable slides.

4. A device for positioning a measuring element according to claim 3, further comprising second threaded spindles for guiding said adjustable slides, said second threaded spindles slideably connected to said first threaded spindles.

5. A device for positioning a measuring element according to claim 4, further comprising drive means connected to said second threaded spindles for driving said second threaded spindles, said drive means drivingly connecting said first and said second threaded spindles.

6. A device for positioning a measuring element according to claim 5, wherein said drive means is a belt drive.

7. A device for positioning a measuring element according to claim 1, further comprising a base plate on which said stepping motors are attached, and wherein said first threaded spindles extend parallel to said base plate, with respective pairs of said first threaded spindles being perpendicular to one another.

8. A device for positioning a measuring element according to claim 1, wherein said first threaded spindles penetrate said stepping motors and are directly drivable by said stepping motors.

9. A device for positioning a measuring element according to claim 1, wherein said first threaded spindles are arranged in pairs parallel to said stepping motors and are drivable by said stepping motors by a driving means.

10. A device for positioning a measuring element according to claim 9, wherein said driving means is a belt drive.

11. A device for positioning a measuring element according to claim 1, further comprising holders connected to said base plate for supporting said stepping motors, said stepping motors being arranged in pairs.

12. A device for positioning a measuring element according to claim 11, further comprising supporting elements connected to said base plate for supporting in a pivotable manner said first threaded spindles.

13. A device for positioning a measuring element according to claim 12, wherein said first threaded spindles are further pivotably supported at said holders.

14. A device for positioning a measuring element according to claim 1, wherein said base plate in the area of the measuring element is provided with a recess.

15. A device for positioning a measuring element according to claim 1, further comprising spring means for connecting at least one of said parallelogram linkage systems to said base plate in a springed manner.

16. A device for positioning a measuring element according to claim 15, wherein said spring means comprises a rail and at least one spring, said spring supporting said rail at said base plate.

* * * * *